US006800055B2

(12) United States Patent
Amols et al.

(10) Patent No.: US 6,800,055 B2
(45) Date of Patent: Oct. 5, 2004

(54) LOW ATTENUATING RADIOACTIVE SEEDS

(75) Inventors: Howard Ira Amols, Bronx, NY (US); Timothy Charles Kiorpes, Doylestown, PA (US); Benjamin David McDaniel, Newport Beach, CA (US); Michael Dennis O'Hara, Stewartsville, NJ (US)

(73) Assignee: Cordis Corporation, Miami Lakes, FL (US)

(*) Notice: Subject to any disclaimer, the term of this patent is extended or adjusted under 35 U.S.C. 154(b) by 159 days.

(21) Appl. No.: 09/790,122

(22) Filed: Feb. 21, 2001

(65) Prior Publication Data

US 2002/0123660 A1 Sep. 5, 2002

(51) Int. Cl.[7] .......................... A61M 36/00; A61N 5/00
(52) U.S. Cl. .................... 600/8; 600/3; 600/4
(58) Field of Search ........................ 600/1–8

(56) References Cited

U.S. PATENT DOCUMENTS

| | | | |
|---|---|---|---|
| 4,323,055 A | 4/1982 | Kubiatowicz | |
| 4,454,795 A | 6/1984 | Ellis | |
| 4,737,153 A | 4/1988 | Shimamura et al. | |
| 4,819,618 A | * 4/1989 | Liprie ........................... | 600/7 |
| 4,994,013 A | 2/1991 | Suthanthiran et al. | |
| 5,059,166 A | 10/1991 | Fischell et al. | |
| 5,163,896 A | 11/1992 | Suthanthiran et al. | |
| 5,199,939 A | 4/1993 | Dake et al. | |
| 5,863,284 A | 1/1999 | Klein | |
| 5,871,436 A | 2/1999 | Eury | |
| 5,873,811 A | 2/1999 | Wang et al. | |
| 5,882,291 A | 3/1999 | Bradshaw et al. | |
| 5,899,882 A | 5/1999 | Waksman et al. | |
| 5,976,067 A | 11/1999 | Tucker et al. | |
| 6,007,475 A | 12/1999 | Slater et al. | |
| 6,019,718 A | 2/2000 | Hektner | |
| 6,036,682 A | 3/2000 | Lange et al. | |
| 6,059,714 A | 5/2000 | Armini et al. | |
| 6,077,213 A | 6/2000 | Ciezki et al. | |
| 6,096,070 A | 8/2000 | Ragheb et al. | |
| 6,103,295 A | 8/2000 | Chan et al. | |
| 6,132,359 A | 10/2000 | Bolenbaugh | |
| 6,149,574 A | 11/2000 | Trauthen et al. | |
| 6,156,046 A | 12/2000 | Passafaro et al. | |
| 6,159,143 A | 12/2000 | Lennox | |
| 6,163,947 A | 12/2000 | Coniglione | |
| 6,248,057 B1 | * 6/2001 | Mavity et al. ................... | 600/3 |
| 6,508,755 B1 | * 1/2003 | Ravins et al. ................... | 600/8 |

FOREIGN PATENT DOCUMENTS

| | | |
|---|---|---|
| WO | WO 97/19706 A | 6/1997 |
| WO | WO 00/59571 A | 10/2000 |
| WO | WO 00/71204 A | 11/2000 |
| WO | WO 01/89632 A | 11/2001 |

OTHER PUBLICATIONS

European Search Report dated Oct. 17, 2003 for corresponding Appln. No. EP 02 25 1168.

* cited by examiner

*Primary Examiner*—Thomas Denion
*Assistant Examiner*—Jaime Corrigan
(74) *Attorney, Agent, or Firm*—Carl Evans

(57) ABSTRACT

A low attenuation radioactive seed utilizing a core having a fluted or non-circular cross section is utilized for increasing the dose rate, decreasing the dwell times and improving the clinical outcomes by increasing the dose consistency throughout the treatment zone. The fluted or non-circular cross section core would increase the surface area for the deposition of the radioactive substance thereby increasing the therapeutic efficacy of the seed. In addition, the fluted or non-circular cross section may be designed in a manner to reduce photon emission attenuation by reducing the distance an inwardly directed photon would have to travel to traverse the core.

6 Claims, 1 Drawing Sheet

LOW ATTENUATING RADIOACTIVE SEEDS

BACKGROUND OF THE INVENTION

1. Field of the Invention

The present invention relates to brachytherapy devices, and more particularly to improved radioactive seeds for use in radiation therapy.

2. Discussion of the Related Art

Percutaneous transluminal coronary angioplasty (PTCA) is a therapeutic medical procedure used to increase blood flow through an artery and is the predominant treatment for coronary vessel stenosis. The increasing popularity of the PTCA procedure is attributable to its relatively high success rate and its minimal invasiveness compared with coronary by-pass surgery. Patients treated utilizing PTCA; however, may suffer from restenosis. Restenosis refers to the re-narrowing of an artery after a successful angioplasty procedure. Restenosis usually occurs within the initial six months after an angioplasty. Early attempts to alleviate the effect of restenosis included repeat PTCA procedures or by-pass surgery, with attendant high cost and added patient risk.

More recent attempts to prevent restenosis by use of drugs, mechanical devices, and other experimental procedures have limited long term success. Stents, for example, dramatically reduce acute reclosure and slow the effects of smooth muscle cell proliferation by enlarging the maximal luminal diameter, but otherwise do nothing substantial to slow the proliferative response to the angioplasty induced injury.

Restenosis is now believed to occur at least in part as a result of injury to the arterial wall during the lumen opening angioplasty procedure. In some patients, the injury initiates a repair response that is characterized by hyperplastic growth of the vascular smooth muscle cells in the region traumatized by the angioplasty. Intimal hyperplasia or smooth muscle cell proliferation narrows the lumen that was opened by the angioplasty, regardless of the presence of a stent, thereby necessitating a repeat PICA or use of other procedures to alleviate the restenosis.

Recent studies indicate that intravascular radiotherapy (IRT) has promise in the prevention or long-term control of restenosis following angioplasty. Intravascular radiotherapy may also be used to prevent or delay stenosis following cardiovascular graft procedures or other trauma to the vessel wall. Proper control of the radiation dosage, however, appears to be important to inhibit or substantially arrest hyperplasia without causing excessive damage to healthy tissue. Underdosing may sometimes result in inadequate inhibition of smooth muscle cell hyperplasia, or even exacerbation of hyperplasia and resulting restenosis.

Radiation therapy may also be utilized in the treatment of other diseases such as cancerous and non-cancerous tumors. In this type of therapy, the ultimate aim is to destroy the malignant tissue without causing excessive radiation damage to nearby healthy, and possibly vital tissue. This is difficult to accomplish because of the proximity of malignant tissue to healthy tissue.

Brachytherapy is a form of radiation treatment in which an ionizing radiation source is placed into or adjacent to a tumor or stenotic lesion. Although any number of radioactive substances and/or radioactive sources may be utilized in brachytherapy, Iodine-125 is currently a good candidate isotope for vascular brachytherapy. Iodine-125 has been used as a liquid or immobilized onto a variety of surfaces for diagnostic and therapeutic purposes. It has already been fashioned into a variety of shapes and used clinically for cancer treatment as briefly described above. One standard method for immobilizing Iodine-125 on to a solid surface is through electroplating. Currently, Iodone-125 is immobilized onto the surface of solid silver wires for a very secure bond. Silver is specifically utilized because of the extremely secure bond it forms with the Iodine-125. In order to ensure the effectiveness of the radiation, the entire radioactive source should contribute photons of radiation. However, in this design, a number of photons produced on one side of the seed or wire may have to travel through the solid stiver wire to be a component of the radiation dose on the other side of the wire or the seed. A difficulty with this is that the solid silver wire attenuates some of these photons that are produced by the Iodine-125 plated on the surface of the silver wire thereby reducing the therapeutic effectiveness. In addition, standard seeds or wires currently utilized have minimal surface area due to size constraints, thereby also reducing the radiation dose.

SUMMARY OF THE INVENTION

The low attenuating radioactive seed design of the present invention provides a means for overcoming the difficulties associated with the treatments and devices as briefly described above.

In accordance with one aspect, the present invention is directed to a radioactive seed. The radioactive seed comprises a core having an outer surface and a radioactive material attached to the outer surface of the core. The core has a predetermined length and multifaceted cross-section.

In accordance with another aspect, the present invention is directed to a low attenuation radioactive seed. The low attenuation radioactive seed comprises a core having an outer surface, a substrate affixed to the outer surface of the core, and a radioactive material attached to the substrate. The core has a predetermined length and a multifaceted cross-section.

In accordance with another aspect, the present invention is directed to a low attenuation radioactive seed. The low attenuation radioactive seed comprises a hollow core having an inner surface and an outer surface, and a radioactive material attached to at least one of the inner and outer surface of the hollow core. The hollow core has a predetermined length and a multifaceted cross-section.

The low attenuating radioactive seeds of the present invention utilize modified cross-section wires to increase the surface area upon which the radioactive substance may be deposited without increasing the overall size of the seed. In addition, the modified cross-section wires are designed in such a manner as to reduce the distance a photon directed inwardly rather than outwardly would have to travel through the wire, thereby reducing attenuation. Accordingly, the low attenuating radioactive seeds will have increased dose rates, decreased dwell times because of the increased dose rates, and improved clinical outcomes by increasing the dose consistency throughout the treatment zone.

The low attenuating radioactive seeds of the present invention comprise a silver wire or silver-plated metallic or non-metallic wire that has a fluted or non-circular cross-section. The wire may be plated with Iodine-125 or other radioactive isotope and used to deliver a therapeutic dose of radiation. The low attenuating radioactive seeds require minimal changes in manufacturing processes over existing seeds, thereby minimizing any significant increases in manufacturing costs. In addition, given that the overall size of the seed remains substantially unchanged, existing delivery devices may be utilized thereby obviating the need for redesigned delivery devices.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
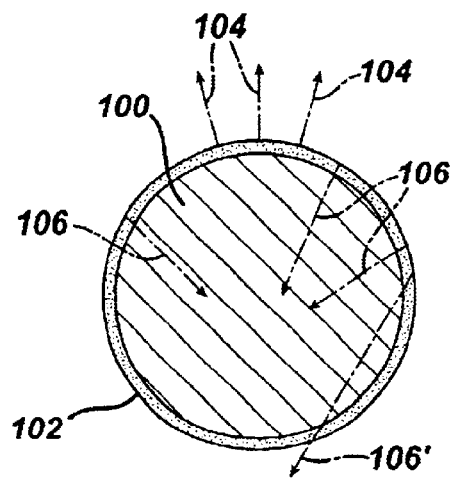
FIG. 1 is a cross sectional view of a currently utilized core wire having a radioactive layer deposited thereon.

The low attenuating radioactive seed of the present invention comprises a therapeutic amount of a radioactive substance appropriately distributed on a carrier body or core disposed in a cavity of a substantially tubular container. The container is sealed at its ends and functions to isolate the radioactive substance from physical or chemical interchange between bodily fluids and the interior of the container, while at the same time permitting the radiation to pass through the walls of the container with minimum attenuation. The container may be delivered to the site of the stenotic lesion or malignant cells by any number of suitable delivery devices which are known in the art.

The basic concept behind the low attenuating radioactive seed of the present invention is to utilize a change in the cross-section of the carrier body or core to increase the surface area of the carrier body for a given length such that a significantly greater amount of radioactive substance may be deposited on the surface of the carrier body. This additional radioactive substance will increase the dose rate, decrease the dwell times, and may improve the clinical outcomes by increasing the dose consistency throughout the treatment zone. In addition, the modified cross-section of the carrier body is preferably designed to reduce the distance an inwardly directed emitted photon would have to traverse through the carrier body, thereby reducing potential attenuation. A more detailed description is given subsequently. The carrier body may be formed from any suitable material which is detectable by x-rays for proper positioning in the body, and to which the requisite therapeutic amount of radioactive material may be attached. In the exemplary embodiments described below, the carrier body or core comprises solid silver wire or silver plated wire, and the radioactive material comprises radioisotopes such as Iodine-125, Iodine-131 and Xenon-133. Other radioactive substances may be utilized. Iodine-125 is preferred because of its energetic emission of photons and its ability to strongly bond with silver.

Silver is the material of choice for a carrier body or core because it provides good x-ray visualization, which is important for proper positioning of the seed during therapy and because radioactive iodine may be easily attached to the surface thereof by chemical or electroplating processes. It is obvious that other x-ray opaque materials such as gold, copper and iron may be plated with silver to form a carrier body equivalent to a solid silver rod for purposes of the present invention. Similarly, silver metal may be deposited, chemically or by using sputtering and ion plating techniques, onto a substrate other than metal, for example, polymers such as polypropylene filament, provided that the thickness of the silver coating on the substrate exceeds about 0.050 mm to ensure adequate x-ray visualization.

Radioactive iodine may be attached to a silver substrate by a variety of suitable means, such as by first chloriding or bromiding the silver to form a layer of insoluble silver chloride or silver bromide, and then replacing the chloride or bromide ions with radioactive iodine ions by simple ion exchange. This process as well as other processes are well known in the relevant art.

Referring to FIG. 1, there is illustrated the cross-sectional design for currently utilized core wires 100. The radioactive layer 102, for example, Iodine-125 may be attached to the core wire 100 utilizing any number of techniques, including the techniques described above. The photons emitted by the Iodine-125 may travel in any direction. As indicated by arrows 104, the emitted photons may travel outwardly from the core wire 100 or they may travel inwardly through the core wire 100 as indicated by arrows 106. As stated above, Iodine-125 is immobilized on to the surface of the solid silver wire in order to ensure a very secure bond thereto and provide good x-ray visualization. However, a difficulty is presented in that the silver core wire 100 attenuates a portion of the emitted photons directed inwardly towards the core 100 as indicated by arrows 106. This attenuation factor is illustrated in FIG. 1 by showing that only a few photons are energetic enough to cross or traverse the entire core 100 as indicated by arrow 106'. Accordingly, a number of these inwardly directed photons never exit the core 100 thereby reducing the therapeutic effectiveness of the seed.

Essentially, the current design illustrated in FIG. 1 poses a number of limitations on the effectiveness of the seed. One limitation involves the attenuation factor of the silver and another limitation involves the substantially circular cross-section of the core wire 100 itself. Emitted photons are capable of traveling through thinner cross-sections of silver; however, when a substantially smaller diameter wire is utilized, there is a proportionate decrease in the available surface area onto which the radioactive material may be deposited, thereby reducing the therapeutic dose. In addition to potentially maximizing the distance an inwardly emitted photon may travel, the substantially circular cross-section of the current design limits the available surface area for radioactive material deposition. Increasing the diameter of the currently utilized core wire is not a viable solution because of the practical limit on the maximum diameter posed by the human vasculature or other interstitial placement of a brachytherapy device.

Figure 2:
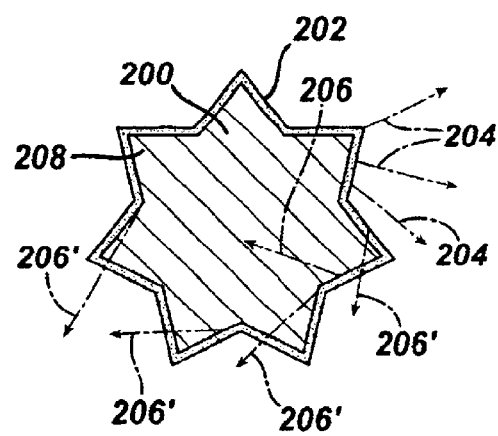
FIG. 2 is a cross sectional view of a first exemplary embodiment of a fluted core wire having a radioactive layer deposited thereon in accordance with the present invention.

The present invention overcomes the limitations described above by utilizing a silver core wire that has a fluted or non-circular cross-sectional design. Referring to FIG. 2, there is illustrated one of any number of exemplary non-circular cross-sectional designs. The silver core 200 illustrated in FIG. 2 may comprise a seven pointed star configuration. The seven pointed star configuration may comprise substantially the same overall diameter as the current design illustrated in FIG. 1, but with significantly increased surface area for the Iodine-125 layer 202, thereby providing for increased emissions of photons indicated by arrows 204. In addition, as described above, a certain number of emitted photons may be directed inwardly, as indicated by arrows 206. However, in this design, the inwardly directed photons may have much shorter distances to traverse through the points 208 of the silver core 200; accordingly, fewer photons would be attenuated and thus increase the therapeutic effectiveness of the device. This is graphically illustrated by the photons indicated by arrow 206', which traverse a much shorter distance than the photons indicated by arrow 206.

Figure 3:
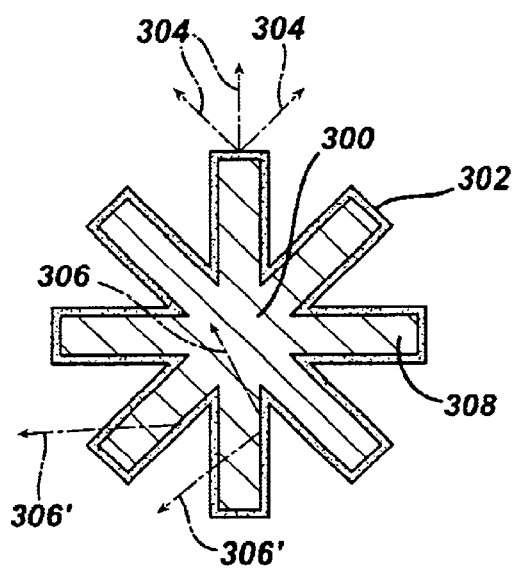
FIG. 3 is a cross sectional view of a second exemplary embodiment of a fluted core wire having a radioactive layer deposited thereon in accordance with the present invention.

FIG. 3 illustrates yet another exemplary embodiment of a fluted core design. In this exemplary embodiment, the core 300 comprises substantially rectangular sections 308 extending from the central core in a hub/spoke type arrangement. This design once again increases the surface area for the Iodine-125 layer 302 while maintaining essentially the same diameter of the currently utilized device illustrated in FIG. 1. In addition, the individual substantially rectangular sections 308 once again decrease the distance through which inwardly directed emitted photons, indicated by arrow 306, would have to travel through the silver core 300, thereby decreasing attenuation. Arrow 306' indicates the photons energetic enough to traverse the shorter distance.

As may be readily appreciated from the foregoing descriptions of the designs illustrated in FIGS. 2 and 3, any number of variations of these designs may be utilized as well as completely different designs to increase the surface area available for the radioactive substance without increasing the overall diameter of the core while limiting the distance any inwardly directed emitted photon would have to travel through the core. For example, the shape and number of flutes, facets or protrusions may be modified. The flutes may be made to form a helix, similar to a thread on a screw or bolt, or pass around the circumference of the wire, like a tread on a tire, or be parallel to the long axis of the core, or any combination of the above designs. In yet another alternate exemplary embodiment, an outer layer of any suitable material may be woven, braided, or wrapped around a core material, or affixed thereto by any known conventional mechanism. The cross section of this material may then be modified to be circular or any other shape that would allow for an increase in the cross-sectional area. This material could be solid, hollow, or layered from different materials and then coated with silver as described above.

Essentially, as described above, the present invention utilizes a modified cross-section, solid silver core wire to increase the radioactive source activity for a given length of wire. Although in the above-described exemplary embodiments a solid silver wire core is described, other core designs may be utilized. For example, any number of suitable materials, including metals and/or polymeric materials may be utilized as the core wire and then coated with a suitably thick layer of silver as described above. Combinations of materials may also be utilized. This type of design would reduce the attenuation factor without having to modify the cross-sectional design if one so chose. In addition, the silver may be varied in thickness and purity to adjust the attenuation. In addition, regardless of whether the core is constructed from silver or other metals or polymers coated with silver, the cores may be constructed as tubular members rather than as solid core structures, thereby decreasing the photon attenuation factor further.

Figure 4:
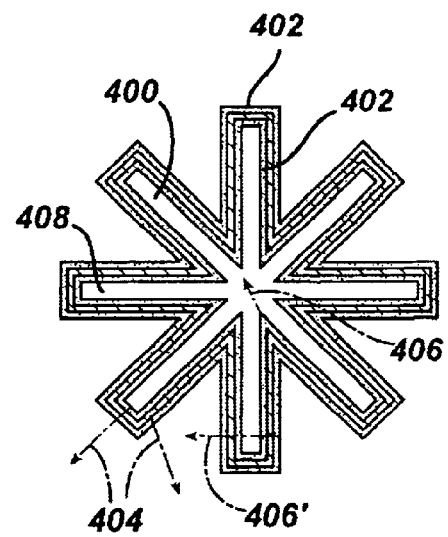
FIG. 4 is a cross sectional view of a third exemplary embodiment of a fluted core wire having a radioactive layer deposited thereon in accordance with the present invention.

FIG. 4 illustrates a tubular hollow core 400 having the cross sectional characteristics of the solid core illustrated in FIG. 3. If a hollow tubular design is utilized, the radioactive iodine layer 402 may be attached on the outside wall or surface of the core 400 as well as on the inside wall or surface of the core 400. Arrows 404 indicate the outwardly directed emitted photons from both radioactive iodine layers 402 and arrows 406 and 406' indicate the inwardly directed emitted photons from both radioactive iodine layers 402. Thus, in addition to decreasing the attenuation, the surface area available for the radioactive substance is effectively doubled.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A radioactive seed comprising:
    a core having a predetermined length and a substantially non-circular, multifaceted cross section for increased surface area and reduced attenuation, the core including a polymeric wire having a silver coating deposited; and
    a radioactive material attached to an outer surface of the core.

2. The radioactive seed according to claim 1, wherein the radioactive material comprises an ionizing radiation source.

3. The radioactive seed according to claim 2, wherein the radioactive material comprises a radioisotope.

4. The radioactive seed according to claim 3, wherein the radioisotope comprises Iodine-125.

5. A low attenuation radioactive seed comprising:
    a core having a predetermined length and a substantially non-circular, multifaceted cross section for increased surface area and reduced attenuation, the core including a polymeric material;
    a silver substrate affixed to an outer surface of the core; and
    a radioactive material attached to an outer surface of the substrate.

6. The low attenuation radioactive seed according to claim 5, wherein the radioactive material comprises Iodine-125.

* * * * *